United States Patent
Wu et al.

(10) Patent No.: US 11,702,444 B2
(45) Date of Patent: Jul. 18, 2023

(54) METHOD FOR PREPARING NATURAL BIOACTIVE PEPTIDE TUBULYSIN U

(71) Applicants: Shenzhen Institute of Geriatrics, Shenzhen (CN); Zhengzhi Wu, Shenzhen (CN)

(72) Inventors: Zhengzhi Wu, Shenzhen (CN); Bohua Long, Shenzhen (CN); Limin Li, Shenzhen (CN); Zhiyue Li, Shenzhen (CN); Zhanyan Liu, Shenzhen (CN)

(73) Assignees: SHENZHEN INSTITUTE OF GERIATRICS, Shenzhen (CN); Zhengzhi Wu, Shenzhen (CN)

( * ) Notice: Subject to any disclaimer, the term of this patent is extended or adjusted under 35 U.S.C. 154(b) by 0 days.

(21) Appl. No.: 17/984,642

(22) Filed: Nov. 10, 2022

(65) Prior Publication Data

US 2023/0099436 A1    Mar. 30, 2023

Related U.S. Application Data

(63) Continuation of application No. PCT/CN2020/139779, filed on Dec. 27, 2020.

(30) Foreign Application Priority Data

May 11, 2020  (CN) .......................... 202010393017.3

(51) Int. Cl.
*C07K 1/00* (2006.01)
*C07K 1/02* (2006.01)
*C07K 1/22* (2006.01)

(52) U.S. Cl.
CPC ............... *C07K 1/026* (2013.01); *C07K 1/22* (2013.01)

(58) Field of Classification Search
CPC ...................................................... C07K 1/22
See application file for complete search history.

(56) References Cited

FOREIGN PATENT DOCUMENTS

CN       111454230 A      7/2020
WO    WO-2015160833 A1 * 10/2015  ........... A61K 31/282

OTHER PUBLICATIONS

Joseph T. Lundquist, IV and Jeffrey C. Pelletier*; "Improved Solid-Phase Peptide Synthesis Method Utilizing r-Azide-Protected Amino Acids"; Organic Letters; 2001; 781-783; vol. 3, No. 5.
Hiromu Hattori et al., "Total Synthesis of Tiacumicin A. Total Synthesis, Relay Synthesis, and Degradation Studies of Fidaxomicin (Tiacumicin B, Lipiarmycin A3)"; The Journal of Organic Chemistry; 2018, 7180-7208.
CNIPA, Notification of a First Office Action for CN202010393017.3, dated Jul. 29, 2021.
Shenzhen Institute of Geriatrics, Zhengzhi Wu (Applicants), Reply to Notification of a First Office Action for CN202010393017.3, w/ (allowed) replacement claims, dated Aug. 2, 2021.
CNIPA, Notification to grant patent right for invention in CN202010393017.3, dated Jan. 19, 2022.

* cited by examiner

*Primary Examiner* — Jeanette M Lieb
(74) *Attorney, Agent, or Firm* — Zhigang Ma

(57) ABSTRACT

A preparation method of a novel natural bioactive peptide Tubulysin U includes: dissolving a compound 2 in trifluoroacetic acid, heating under reflux to prepare an intermediate, reacting with a compound 3 and N,N-diisopropylethylamine to obtain a product, reacting the product with 2,6-dimethylpyridine and tert-butyldimethylsilyl trifluoromethanesulfonate, adding sodium hydroxide after the reaction to prepare an intermediate acid, reacting the intermediate acid with a compound 6, HATU and N,N-diisopropylethylamine to obtain a product, adding triphenylphosphine to prepare an intermediate amine, adding a compound 8 and HATU to react, adding ammonium fluoride to prepare a first intermediate, adding sodium hydroxide to the first intermediate to prepare a second intermediate, adding acetic anhydride to the second intermediate to prepare a third intermediate, adding trifluoroacetic acid to the third intermediate to prepare a fourth intermediate, and adding formaldehyde and sodium cyanoborohydride to the fourth intermediate to react, thereby obtaining a target product.

20 Claims, No Drawings

METHOD FOR PREPARING NATURAL BIOACTIVE PEPTIDE TUBULYSIN U

TECHNICAL FIELD

The disclosure relates to the field of drug synthesis technologies, in particular to a method for preparing a natural bioactive peptide Tubulysin U.

BACKGROUND

The tetrapeptide compounds Tubulysins were extracted from Myxobacteria for 2000 years, but their crystal structures were determined until 2004. Tubulysins A-Z are a family of compounds (see Table 1), which all belong to natural products, and can be represented by the following chemical structural formula:

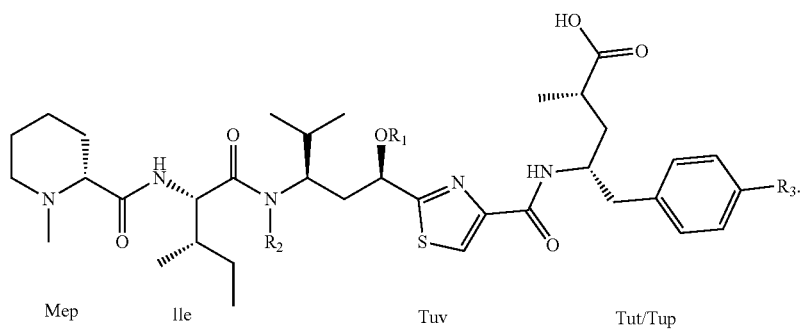

TABLE 1

Structural Formula of Tubulysins Family Compounds

| Tubulysin | $R_1$ | $R_2$ | $R_3$ |
|---|---|---|---|
| A | Ac | $CH_2OC(O)CH_2CH(CH_3)_2$ | OH |
| B | Ac | $CH_2OC(O)CH_2CH_2CH_3$ | OH |
| C | Ac | $CH_2OC(O)CH_2CH_3$ | OH |
| D | Ac | $CH_2OC(O)CH_2CH(CH_3)_2$ | H |
| E | Ac | $CH_2OC(O)CH_2CH_2CH_3$ | H |
| F | Ac | $CH_2OC(O)CH_2CH_3$ | H |
| G | Ac | $CH_2OC(O)CH_2=C(CH_3)_2$ | OH |
| H | Ac | $CH_2OC(O)CH_3$ | H |
| I | Ac | $CH_2OC(O)CH_3$ | OH |
| U | Ac | H | H |
| V | H | H | H |
| Z | H | H | OH |

Studies find that Tubulysin U exhibits extremely effective cytotoxic activity in mammalian cells, including multi-drug resistance cell lines, and $IC_{50}$ (i.e., half maximal inhibitory concentration) values are in a lower nano-molar range (see Table 2). Tubulysin U is a cytotoxic active tubulin lysins that inhibits tubulin polymerization and leads to cell cycle arrest and apoptosis. In addition, studies show that Tubulysin U also has advantages of inhibiting angiogenesis and resisting multiple drug resistance. Compared with other anti-cancer drugs, Tubulysin U has obvious advantages in terms of water solubility, and shows super-strong anti-cancer activity on specific cancer cells, so that Tubulysin U becomes one of most loved target molecules in research and development of novel anti-cancer drugs.

TABLE 2

Antiproliferative activity in vitro of Tubulysin U on human cancer cells

| Human cancer cells | $IC_{50}$ (nM) |
|---|---|
| 1A9 ovarian cancer cells | 0.65 |
| MCF-7 breast cancer cells | 0.4 |

From the very short development history of Tubulysin U, Tubulysin U is subject to more and more people's attention with its unique biological activity, and may become a star molecule in anti-tumor drugs in several years in the future.

However, in the prior art, the synthesis thereof is not ideal, there are dozens of documents reported on the chemical synthesis of Tubulysin U and analogues thereof, but most of the synthetic routes are not perfect, and there is a great further exploration space. How to find a simple, rapid and mass-synthesized route is of great significance for further biological research and clinical application of Tubulysin U as soon as possible.

SUMMARY

An object of the present disclosure is to provide a novel preparation method of a natural bioactive peptide Tubulysin U, the synthetic route of the preparation method conforms to a green chemical standard, renewable and recyclable resources are utilized as much as possible, the toxicity of the used reagents are small, and the environmental pollution is very small after the reaction is treated. In particular, the preparation method has high total yield, good stereoselectivity, convenient experimental operation, mild reaction conditions, simple separation and purification, and can be used for large-scale preparation.

In order to achieve the above effects, the basic concept of technical solutions adopted by the present disclosure are as follows:

A preparation method of a natural bioactive peptide Tubulysin U, the preparation method adopts a route as follows:

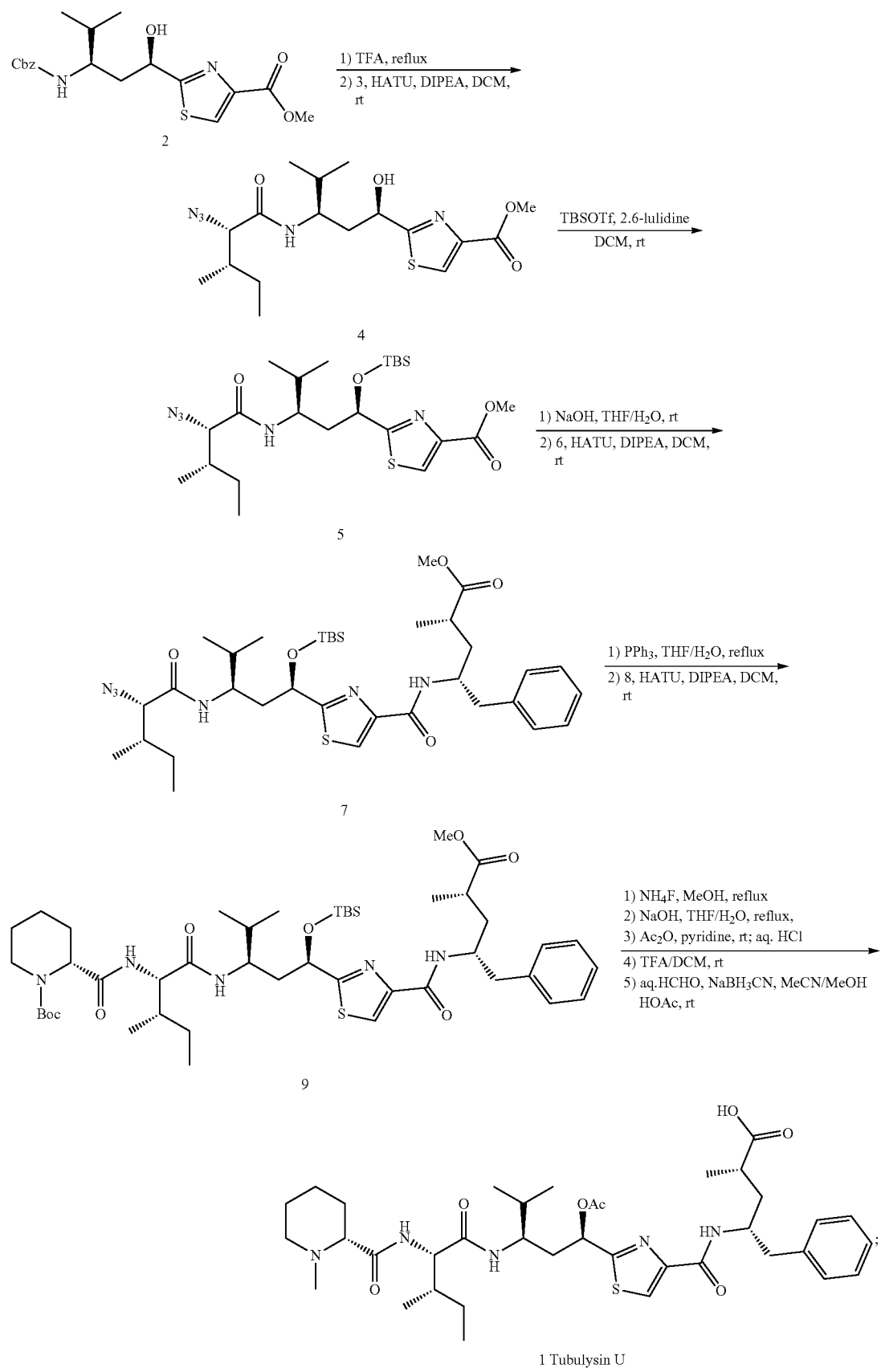

wherein structural formulas of the compound 3, the compound 6 and the compound 8 used in the above route respectively are as follows:

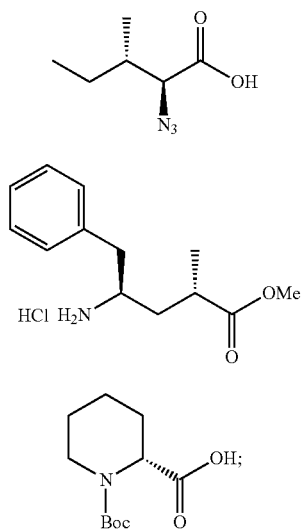

the preparation method includes the following steps:

step 1, dissolving the compound 2 in trifluoroacetic acid (abbreviated as TFA), heating under reflux, and preparing an intermediate;

dissolving the intermediate in anhydrous dichloromethane (abbreviated as DCM) to obtain first solution, adding the compound 3 and N,N-diisopropylethylamine (abbreviated as DIPEA) into the first solution, and reacting at room temperature to prepare the compound 4;

step 2, dissolving the obtained compound 4 in dried DCM to obtain second solution, adding 2,6 -lutidine and tert-butyldimethylsilyl trifluoromethanesulfonate (abbreviated as TBSOTf) into the second solution under ice water bath cooling and reacting at room temperature to prepare the compound 5;

step 3: dissolving the compound 5 in the mixed solvent of tetrahydrofuran and water to obtain third solution, adding the sodium hydroxide (its chemical formula is NaOH) solid into the third solution under ice-water bath cooling, and reacting at room temperature to prepare an intermediate acid;

dissolving the obtained intermediate acid in anhydrous DCM to obtain fourth solution, adding the compound 6 and 2-(7-Azabenzotriazol-1-yl)-N,N,N',N'-tetramethyluronium hexafluorophosphate (abbreviated as HATU) into the fourth solution, uniformly stirring, dropwise adding DIPEA, and reacting at room temperature to prepare the compound 7;

step 4, dissolving the obtained compound 7 in the mixed solvent of tetrahydrofuran and water to obtain fifth solution, adding triphenylphosphine (abbreviated as PPh$_3$) into the fifth solution, heating under reflux, and preparing an intermediate amine;

dissolving the intermediate amine in anhydrous DCM to obtain sixth solution, adding the compound 8 and the HATU into the sixth solution, uniformly stirring, dropwise adding DIPEA, and reacting at room temperature to prepare compound 9;

step 5, dissolving the compound 9 in methanol (its chemical formula is MeOH) to obtain seventh solution, adding the ammonium fluoride (its chemical formula is NH$_4$F) solid into the seventh solution, heating under reflux and reacting overnight, and performing post-treatment to obtain a first intermediate;

dissolving the first intermediate in the mixed solvent of tetrahydrofuran and water to obtain eighth solution, adding the sodium hydroxide solid into the eighth solution, then heating under reflux, and performing post-treatment to obtain a second intermediate;

dissolving the second intermediate in pyridine to obtain ninth solution, then adding acetic anhydride (its chemical formula is Ac$_2$O) into the ninth solution, reacting at room temperature, and performing post-treatment to obtain a third intermediate;

dissolving the third intermediate in DCM to obtain tenth solution, then adding trifluoroacetic acid (abbreviated as TFA), reacting at room temperature, and performing post-treatment to obtain a fourth intermediate;

dissolving the fourth intermediate in the mixed solvent of methyl cyanide and methanol (i.e., MeCN/MeOH) to obtain eleventh solution, adding the formaldehyde (i.e., HCHO) into the eleventh solution, reacting at room temperature for a certain time, then adding sodium cyanoborohydride (its chemical formula is NaBH$_3$CN) to continue the reaction, and performing post-treatment to obtain a target product (i.e., Tubulysin U).

In an embodiment, in the preparation method of the natural bioactive peptide Tubulysin U, the compound 6 is synthesized through a synthetic route as follows:

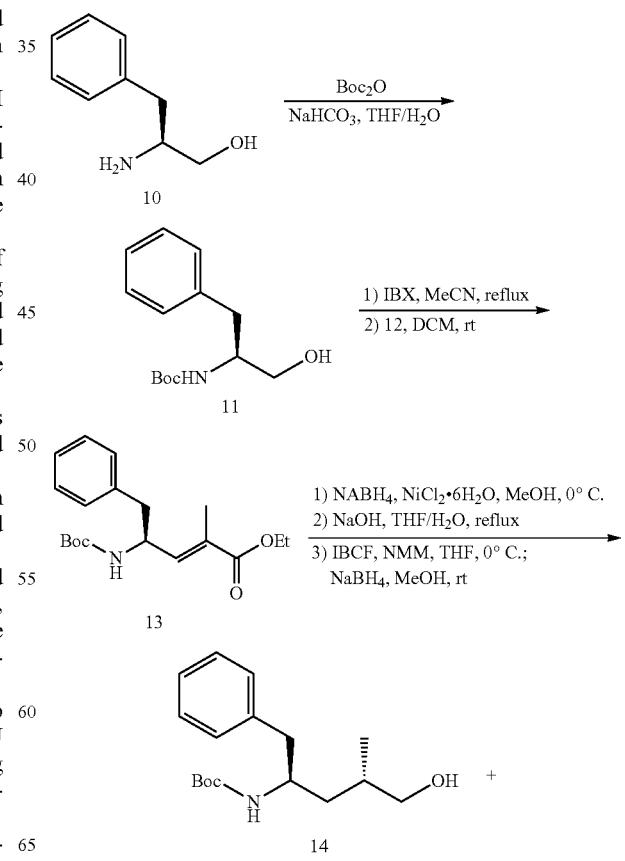

-continued

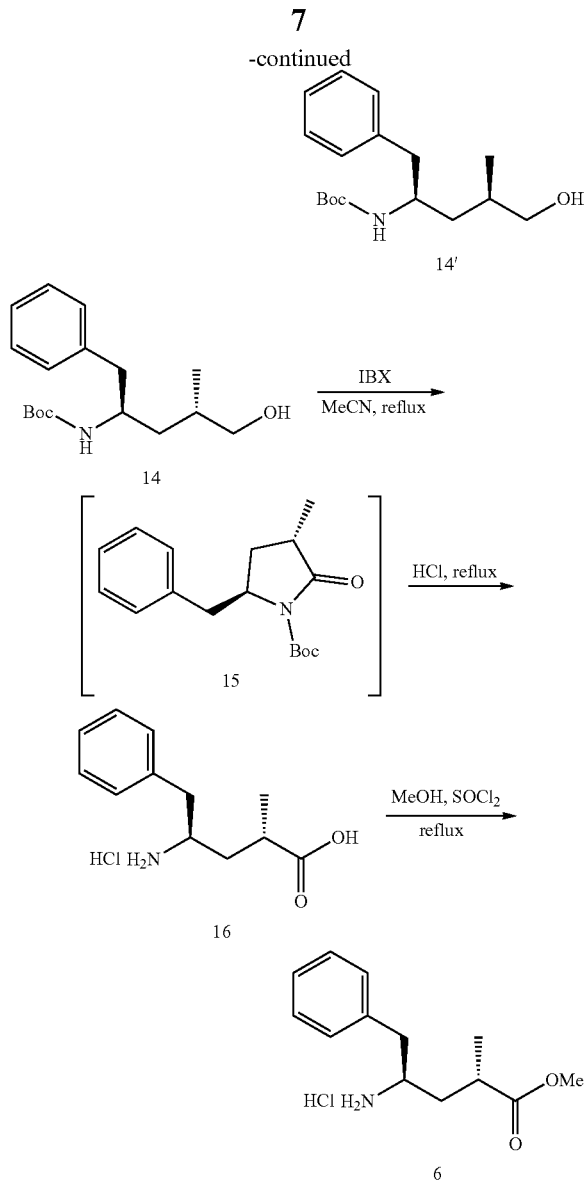

wherein a structural formula of the compound 12 used in the above synthetic route is as follows:

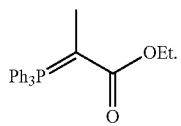

In an embodiment, the step 1 includes:

step 11: dissolving the compound 2 in the TFA, heating under reflux, and performing vacuum concentration to obtain the intermediate;

step 12: dissolving the intermediate in the anhydrous DCM to obtain the first solution, adding the compound 3 into the first solution and uniformly stirring, then dropwise adding DIPEA and stirring for reaction at room temperature, quenching the reaction after the reaction is completed, extracting organic phases with DCM and combining the extracted organic phases, washing the combined organic phases with water and saturated salt water in sequence, collecting and drying the washed organic phases, concentrating the dried organic phases, and separating by column chromatography the concentrated organic phases to obtain the compound 4.

Preferably, in the step 1, time of the heating under reflux is 2-4 h, more preferably 3 h.

Preferably, in the step 1, a molar ratio of the compound 2:the compound 3:the HATU:the DIPEA is 1:1.1-1.4:2-3:4-5, more preferably 1:1.1:2:4.

Preferably, in the step 12, column chromatography separation is performed on the concentrated organic phases by using eluent of a petroleum ether:ethyl acetate in a volume ratio of 4:1.

In an embodiment, the step 2 includes:

dissolving the obtained compound 4 in the dried DCM to obtain the second solution, adding 2,6-lutidine and TBSOTf into the second solution to obtain a mixture under ice-water bath cooling, then heating the mixture to room temperature for reaction, adding water for quenching the reaction after the reaction is completed, extracting organic phases with DCM and combining the extracted organic phases, using diluted hydrochloric acid and saturated salt water sequentially for washing the combined organic phases, collecting the washed organic phases by liquid separation and drying the collected organic phases through anhydrous sodium sulfate, concentrating the dried organic phases, and separating the concentrated organic phases through chromatography separation to obtain the compound 5.

Preferably, a molar ratio of the compound 4:2,6-lutidine:TBSOTf is 1:3-4:1.2-2, more preferably 1:3:1.5.

Preferably, in the step 2, the concentrated organic phases are separated through the column chromatography with eluent of a volume ratio of petroleum ether:ethyl acetate being 8:1.

In an embodiment, the step 3 includes:

dissolving the compound 5 in the mixed solvent of tetrahydrofuran and water to obtain the third solution, adding sodium hydroxide solid under ice-water bath cooling into the third solution, heating to room temperature and stirring for reaction, then cooling in ice water bath and adjusting pH of reaction solution to 2, afterwards extracting organic phases with ethyl acetate and combining the extracted organic phases, washing the combined organic phases with water and saturated salt water in sequence, drying the washed organic phases by adding anhydrous sodium sulfate after separating liquid, and performing vacuum concentration on the dried organic phases to obtain the intermediate acid;

dissolving the obtained intermediate acid in the anhydrous DCM to obtain the fourth solution, adding the compound 6 and HATU into the fourth solution and uniformly stirring, then dropwise adding DIPEA and stirring for reaction at room temperature, adding water for quenching the reaction after the reaction is completed, extracting organic phases with DCM and combining extracted organic phases, washing the combined organic phases with water and saturated salt water in sequence, drying the washed organic phases by adding anhydrous sodium sulfate after separating liquid, performing vacuum concentration on the dried organic phases, and then performing column chromatography separation on the concentrated organic phases with the eluent of petroleum ether:ethyl acetate being 6:1 to obtain the oily compound 7.

Preferably, a volume ratio of tetrahydrofuran:water in the mixed solvent of tetrahydrofuran and water is 1:1

Preferably, the molar ratio of compound 5:compound 6:HATU:N,N-diisopropylethylamine is 1:1.1-1.5:2-3:4-5, more preferably 1:1.1:2.5:5.

In an embodiment, the step 4 includes:

dissolving the obtained compound 7 in the mixed solvent of tetrahydrofuran and water to obtain fifth solution, adding the $PPh_3$ into the fifth solution, heating under reflux for reaction, performing vacuum concentration, washing with toluene to remove water, and performing vacuum drying to obtain the intermediate amine;

dissolving the intermediate amine in the anhydrous DCM to obtain the sixth solution, adding the compound 8 and the HATU into the sixth solution and uniformly stirring, then dropwise adding DIPEA and stirring for reaction at room temperature, adding water for quenching the reaction after the reaction is completed, extracting organic phases with DCM and combining the extracted organic phases, washing the combined organic phases with water and saturated salt water in sequence, drying the washed organic phases by adding anhydrous sodium sulfate after separating liquid, performing vacuum concentration on the dried organic phases, and then performing column chromatography separation on the concentrated organic phases by using petroleum ether and ethyl acetate as eluent to obtain the oily compound 9.

Preferably, a molar ratio of the compound 7:the compound 8:the HATU:the DIPEA is 1:1.1-1.5:2-3:4-6, more preferably 1:1.3:3:6.

Preferably, in the step 4, a volume ratio of the tetrahydrofuran:the water in the mixed solvent of tetrahydrofuran and water is 20:1.

Preferably, in the step 4, the $PPh_3$ is added, and the heating under reflux is performed for 1.5-2.5 h, more preferably 2 h.

In an embodiment, the step 5 includes:

dissolving the compound 9 in methanol to obtain the seventh solution, adding ammonium fluoride solid into the seventh solution, heating under reflux for reaction overnight, performing vacuum concentration, adding water for dilution, extracting organic phases with ethyl acetate and combining the extracted organic phases, washing the combined organic phases with saturated salt water, drying the washed organic phases by adding anhydrous sodium sulfate after separating liquid, and performing vacuum concentration on the dried organic phases to obtain the first intermediate;

dissolving the first intermediate in the mixed solvent of tetrahydrofuran and water with a volume ratio of tetrahydrofuran:water being 1:1 to obtain the eight solution, adding the sodium hydroxide solid into the eight solution, then heating under reflux for reaction, cooling in ice water bath, adjusting the pH of the reaction solution to 2, subsequentially extracting organic phases with ethyl acetate and combining the extracted organic phases, washing the combined organic phases with water and saturated salt water in sequence, drying the washed organic phases with anhydrous sodium sulfate after separating liquid, and performing vacuum concentration on the dried organic phases to obtain the second intermediate;

dissolving the second intermediate in pyridine to obtain the ninth solution, then adding acetic anhydride into the ninth solution and stirring for reaction at room temperature, adding water for quenching the reaction after the reaction is completed, then cooling in ice water bath and adjusting the pH of the reaction solution to 2, subsequentially extracting organic phases with ethyl acetate and combining the extracted organic phases, washing the combined organic phases with water and saturated salt water in sequence, drying the washed organic phases with anhydrous sodium sulfate after separating liquid, and performing vacuum concentration on the dried organic phases to obtain the third intermediate;

dissolving the third intermediate in DCM to obtain the tenth solution, then adding TFA into the tenth solution and stirring for reaction at room temperature, performing vacuum concentration and vacuum drying to obtain the fourth intermediate;

dissolving the fourth intermediate in the mixed solvent of methyl cyanide and methanol with a volume ratio of methyl cyanide:methanol being 1:1 to obtain the eleventh solution, adding the formaldehyde into the eleventh solution and stirring for reaction at room temperature, then adding sodium cyanoborohydride to continue the reaction, adjusting the pH of the reaction solution to 5, then stirring and reacting overnight at room temperature, performing vacuum concentration, separating and purifying with silica gel column chromatography, and then pulping and purifying with isopropyl ether to obtain the target compound 1 (i.e., Tubulysin U).

Preferably, a molar ratio of the compound 9:the ammonium fluoride is 1:50.

Preferably, the first intermediate:the sodium hydroxide is 1:10.

Preferably, the second intermediate:the acetic anhydride is 1:50.

Preferably, in the step 5, the separating and purifying with silica gel column chromatography use a mobile phase with a volume ratio of methanol:dichloromethane being 1:10.

Preferably, the concentration of the formaldehyde is 37 weight percent (wt %).

In an embodiment, the compound 2 is prepared through a method as follows:

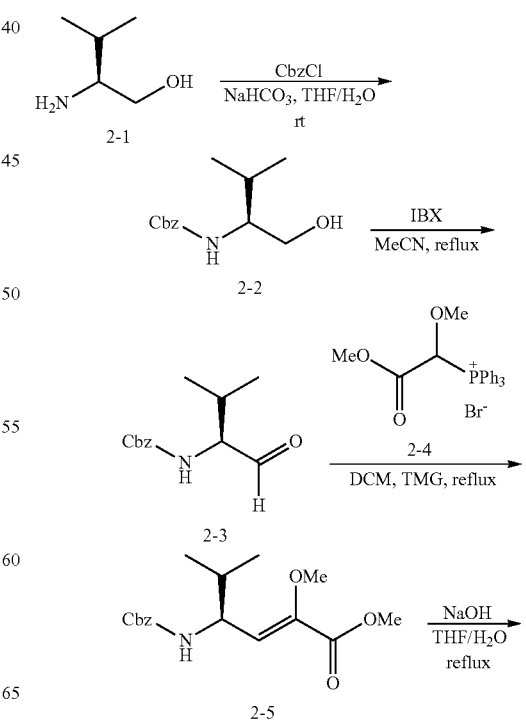

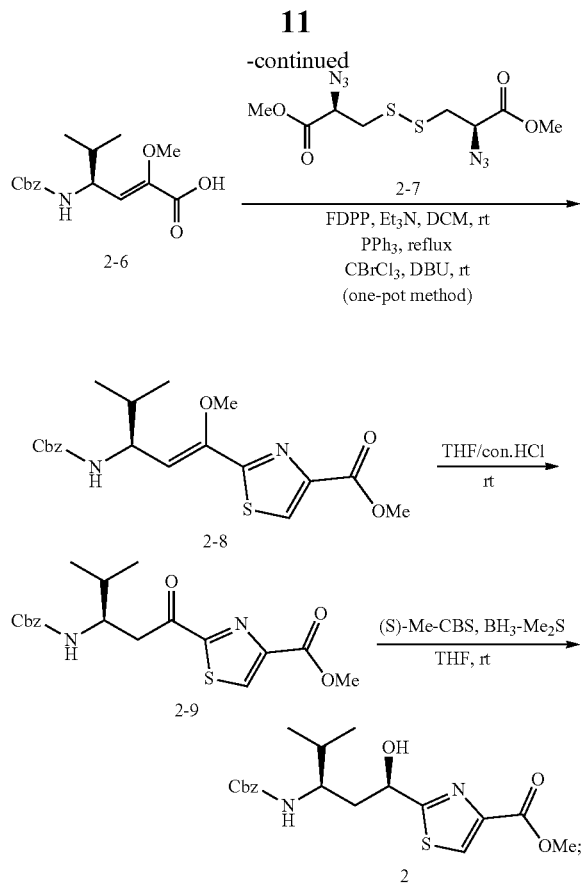

wherein the method includes the following steps:

step 1, dissolving the initial raw material L-valine 2-1 in the mixed solvent of tetrahydrofuran and water, adding the sodium bicarbonate (its chemical formula is NaHCO$_3$) solid and benzyl chloroformate (its chemical formula is CbzCl), and reacting overnight at room temperature to obtain the compound 2-2;

step 2: dissolving the compound 2-2 obtained in step 1 in methyl cyanide (its chemical formula is MeCN), adding 2-iodoxybenzoic acid (abbreviated as IBX), heating under reflux, and obtaining the intermediate aldehyde 2-3;

dissolving the intermediate aldehyde 2-3 in DCM, adding the Wittig reagent 2-4 and 1,1,3,3-tetramethylguanidine (abbreviated as TMG), heating under reflux, and obtaining the compound 2-5;

step 3, dissolving the compound 2-5 in a mixed solvent of tetrahydrofuran and water, adding the sodium hydroxide solid, heating under reflux, and obtaining the compound 2-6;

taking the compound 2-6 as a reaction substrate, adding the coupling reagent and the PPh$_3$ to react with the compound 2-7 to prepare a thiazoline intermediate, then adding the oxidation reagent, and synthesizing the compound 2-8 by a one-pot method;

step 4, dissolving the compound 2-8 in tetrahydrofuran (abbreviated as THF), adding concentrated hydrochloric acid, and reacting at room temperature to obtain the compound 2-9;

step 5: dissolving the compound 2-9 in anhydrous THF under the protection of an inert gas, adding (S)-Me-CBS and borane dimethyl sulfide complex (abbreviated as BH$_3$-Me$_2$-S) under ice water bath cooling, and heating to room temperature for reaction to obtain the compound 2.

In an embodiment, in the preparation method of the compound 2:

in the step 1, a molar ratio of the L-valine 2-1:the sodium bicarbonate:the benzyl chloroformate is 1:3-5:1-1.02, preferably 1:3:1.

Preferably, a reaction time of the step 1 is 10-15 h, more preferably 12 h, after the reaction is completed, vacuum concentration is performed, ethyl acetate is used for extraction, the organic phases are combined and washed with saturated salt water, the washed organic phases are collected by liquid separation, then the collected organic phases are dried by adding anhydrous sodium sulfate, the dried organic phases are filtered, concentrated and drained, and then the compound 2-2 is obtained.

In an embodiment, in the preparation method of the compound 2:

in the step 2, a molar ratio of the compound 2-2:the 2-iodoxybenzoic acid:the Wittig reagent 2-4 is 1:2-3:1.2-1.5, preferably 1:2:1.5.

The technical solutions provided by the present disclosure has the following beneficial effects:

1. The present disclosure provides a novel route to optimize the full synthesis process of natural bioactive peptide Tubulysin U.

2. The synthetic route of the present disclosure conforms to the green chemical standard, and the renewable recyclable resources are used as reaction raw materials, so that the used reagents are low in toxicity, and the environmental pollution is very small after the reaction is treated.

3. The preparation method of the present disclosure has high total yield, good stereoselectivity, convenient experimental operation, mild reaction conditions, simple separation and purification, and can be used for mass preparation, etc.

DETAILED DESCRIPTION OF EMBODIMENTS

In order to make the objectives, technical solutions and advantages of the embodiments of the present disclosure clearer, the technical solutions of the embodiments of the present disclosure are clearly and completely described below. Apparently, the described embodiments are some of the embodiments of the present disclosure rather than all of the embodiments. All other embodiments obtained by those of ordinary skill in the art based on the described embodiments of the present disclosure without creative efforts shall fall within the scope pf protection of the present disclosure.

In the present disclosure, HATU is an abbreviation of 2-(7-azabenztriazole)-N,N,N',N'-tetramethyl urea hexafluorophosphate; DIPEA is an abbreviation of N,N-diisopropylethylamine; DCM is an abbreviation of dichloromethane; and TBSOTf is an abbreviation of tert-butyldimethylsilyl trifluoromethanesulfonate. The English abbreviations of other chemical reagents used are all conventional meanings in the art.

Embodiment 1

According to a basic idea of the present disclosure, this embodiment provides a method for preparing a natural bioactive peptide Tubulysin U. The route of the preparation method is as follows:

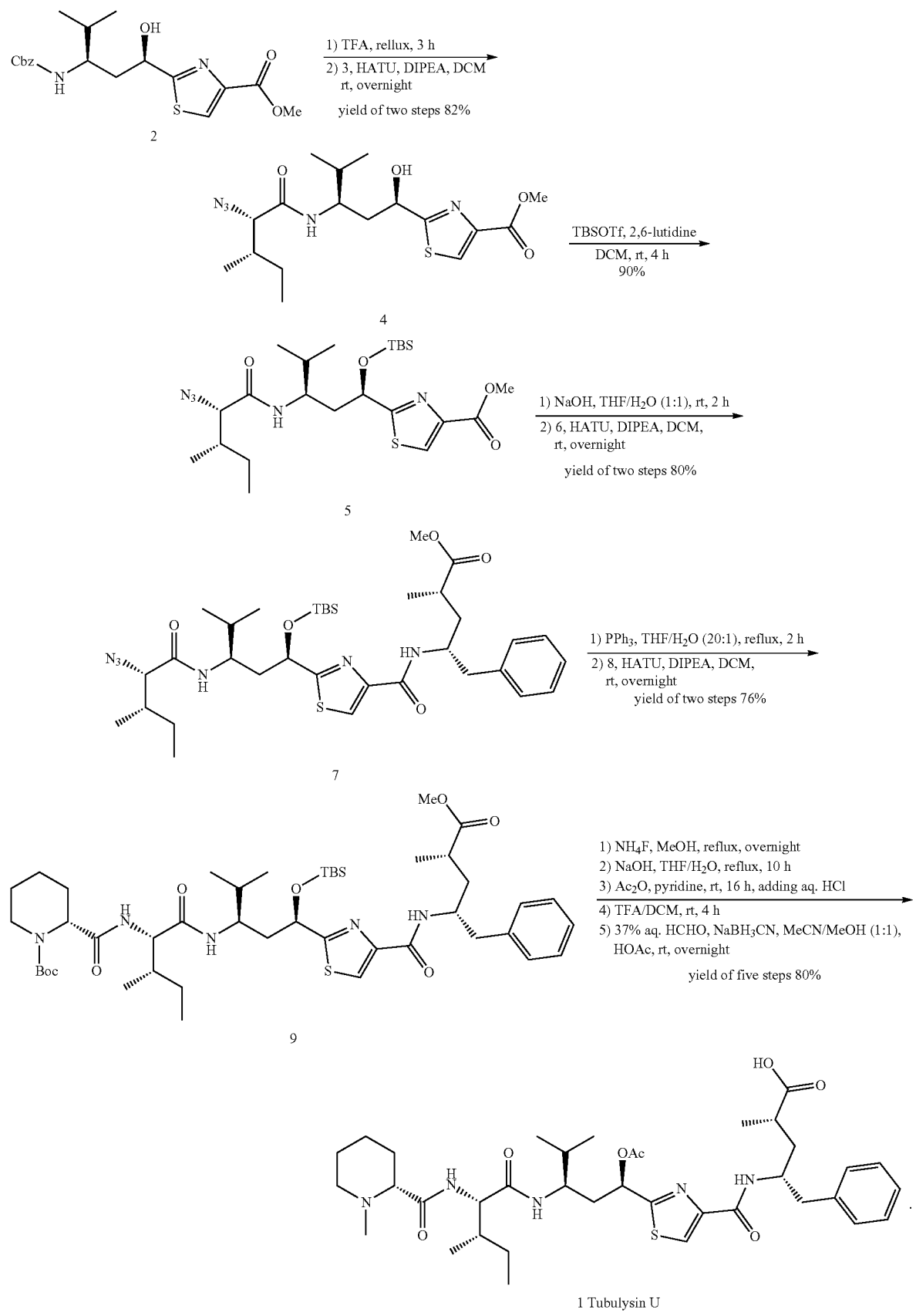

Among them, the structural formulas of the compound 3, compound 6 and compound 8 used in the above route are as follows:

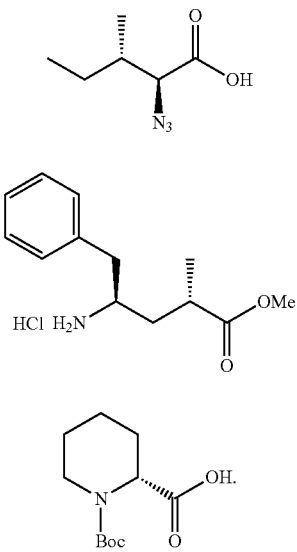

The compound 6 in the above route is synthesized through a route as follows:

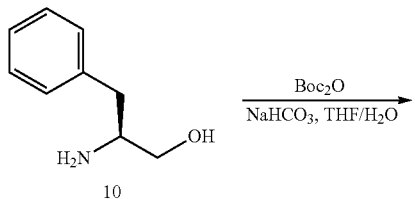

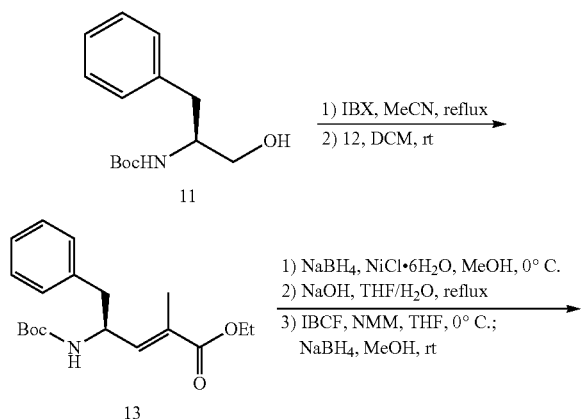

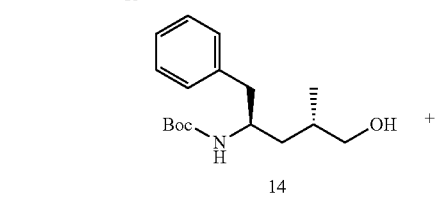

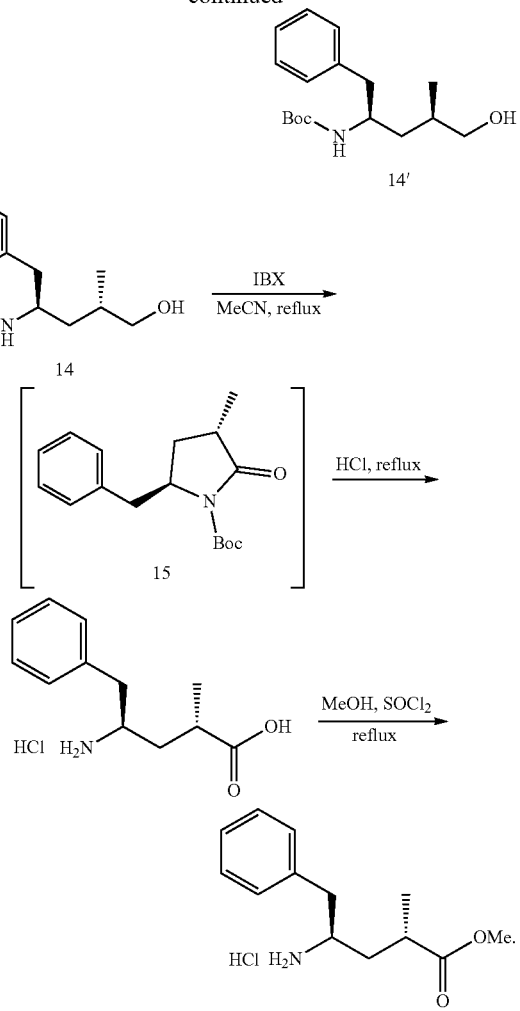

Among them, the structural formula of the compound 12 used in the above route is as follows:

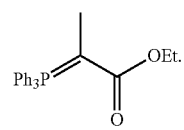

In combination with the above preparation routes, the preparation method of Tubulysin U, i.e., the compound 1 is described in detail below, which includes steps as follows:

(1) Synthesis of Compound 4

The compound 2 (2.0 g, 5.1 mmol) is dissolved in TFA (50 mL) for reaction, heating under reflux for 3 h, follows by vacuum concentration and vacuum drying to obtain the intermediate.

The above intermediate is dissolved in anhydrous DCM (100 mL), the compound 3 (0.86 g, 5.5 mmol) and HATU (3.8 g, 10 mmol) are added and uniformly stirred, then DIPEA (3.3 mL, 20 mmol) is dropwise added and stirred, the reaction is carried out overnight at room temperature, water (200 mL) is added for quenching the reaction, extraction is carried out with DCM for three times, organic phases are combined and washed with water (200 mL) and saturated salt water (200 mL) in sequence, the washed organic phases are dried by adding anhydrous sodium sulfate after separating liquid, the vacuum concentration is carried out to obtain a crude product, and the compound 4 is obtained by rapid column chromatography separation of the crude product by using the eluent of petroleum ether:ethyl acetate being 4:1. The compound 4 is oil with 1.66 g, and the total yield of above two steps is 82%.

The synthesized compound 4 is detected by $^1$H nuclear magnetic resonance ($^1$HNMR), $^{13}$C nuclear magnetic resonance ($^{13}$CNMR) and high resolution mass spectroscopy (HRMS), and the synthesized compound 4 is a pure compound, and each performance index or characterization data thereof is as follows:

$[\alpha]_D^{25}$+5.8 (c0.85, CHCl$_3$); $^1$H NMR (400 MHz, CDCl$_3$) δ8.14 (s, 1H), 6.58 (d, J=9.2 Hz, 1H), 4.88 (dd, J=11.2, 2.4 Hz, 1H), 4.01 (m, 2H), 3.93 (s, 3H), 2.23-2.12 (m, 2H), 1.90-1.76 (m, 2H), 1.47-1.39 (m, 1H), 1.35-1.27 (m, 1H), 1.08 (d, J=7.0 Hz, 3H), 0.99-0.91 (m, 9H); $^{13}$C NMR (101 MHz, CDCl$_3$) δ176.38, 170.75, 161.96, 146.45, 127.64, 69.62, 68.74, 52.35, 51.58, 41.13, 38.49, 31.87, 24.21, 19.61, 18.26, 15.96, 11.60; high resolution electrospray ionization mass spectroscopy (abbreviated as HR-ESIMS) m/z: theoretical calculated value C$_{17}$H$_{27}$N$_5$O$_4$SNa$^+$[M+Na]$^+$: 420.1784, detection value: 420.1789.

The compound 2 used in the above process may be specifically obtained according to the preparation method described in Chinese patent application with application number 202010336478.7. The compound 3 is prepared by the preparation method of the reference document: Organic Letters, 2001, 3(5): 781-783.

(2) Synthesis of Compound 5

The compound 4 (1.66 g, 4.18 mmol) is dissolved in the dried DCM (100 mL), the 2,6-lutidine (1.5 mL, 12.88 mmol) and TBSOTf (1.45 mL, 6.27 mmol) are added under ice-water bath cooling conditions, after 30 min, the reaction temperature is heated to room temperature, the reaction substances are stirred and reacted for 4 h, water (200 mL) is added for quenching the reaction, extraction is carried out with DCM (200 mL) for three times, the extracted organic phases are combined and washed with 1 mol/L (M) dilute hydrochloric acid (200 mL) and saturated saline (200 mL) in sequence, the washed organic phases are dried by adding anhydrous sodium sulfate after separating liquid, then vacuum concentration is performed on the dried organic phases to obtain a crude product, and the compound 5 is obtained by rapid column chromatography separation of the crude product by using the eluent of petroleum ether:ethyl acetate being 8:1. The compound 5 is an oil with 1.93 g and the yield is 90%.

The synthesized compound 5 is detected by $^1$HNMR, $^{13}$CNMR and HRMS, and the synthesized compound 5 is a pure compound, and each performance index or characterization data thereof is as follows:

$[\alpha]_D^{25}$+10.4 (c1.2, CHCl$_3$); $^1$H NMR (400 MHz, CDCl$_3$) δ8.12 (s, 1H), 6.65 (d, J=8.6 Hz, 1H), 5.09 (dd, J=6.6, 5.2 Hz, 1H), 4.02 (d, J=13.2 Hz, 1H), 3.94 (s, 3H), 3.85 (d, J=4.4 Hz, 1H), 2.11 (dd, J=9.3, 6.8 Hz, 1H), 1.95-1.87 (m, 3H), 1.49-1.41 (m, 1H), 1.29 (m, 1H), 1.04 (d, J=6.9 Hz, 3H), 0.94 (s, 9H), 0.91-0.80 (m, 9H), 0.12 (s, 3H), −0.05 (s, 3H); $^{13}$C NMR (101 MHz, CDCl$_3$) δ178.32, 168.53, 161.79, 146.28, 127.49, 70.39, 69.96, 52.41, 51.07, 40.11, 38.26, 31.63, 25.67, 24.22, 18.30, 17.96, 17.24, 17.24, 15.95, 11.48, −4.74, −5.17; HR-ESIMS m/z: theoretical calculated value C$_{23}$H$_{41}$N$_5$O$_4$SSiNa$^+$[M+Na]$^+$: 534.2649, detection value: 534.2653.

(3) Synthesis of Compound 7

The compound 5 (1.93 g, 3.77 mmol) is dissolved in mixed solvent of tetrahydrofuran and water (1:1, 200 mL), the sodium hydroxide solid (1.6 g, 40 mmol) is added under ice water bath cooling, after 30 min, it is heated to room temperature and stirred for reaction for 2 h, after cooling in ice water bath, the diluted hydrochloric acid is added until the pH value of the solution is equal to 2, extraction is performed with ethyl acetate (200 mL) for three times, the extracted organic phases are combined and washed with water (200 mL) and saturated salt water (200 mL) in sequence, the washed organic phases are dried by adding anhydrous sodium sulfate after separating liquid, and vacuum concentration is performed on the dried organic phases to obtain an intermediate acid.

the intermediate acid is dissolved in anhydrous DCM (100 mL), the compound 6 (1.03 g, 4 mmol) and HATU (3.8 g, 10 mmol) are added and uniformly stirred, the DIPEA (3.3 mM, 20 mmol) is dropwise added and stirred, the reaction is carried out overnight at room temperature, water (200 mL) is added for quenching the reaction, extraction is carried out with DCM (200 mL) for three times, the extracted organic phases are combined and washed with water (200 mL) and saturated salt water (200 mL) in sequence, the washed organic phases are dried by adding anhydrous sodium sulfate after separating liquid, vacuum concentration is performed on the dried organic phases to obtain a crude product, and the compound 7 is obtained by rapid column chromatography separation of the crude product by using the eluent of petroleum ether:ethyl acetate being 6:1. The compound 7 is oil with 2.11 g, and the total yield of the above two steps is 80%.

The synthesized compound 7 is detected by $^1$HNMR, $^{13}$CNMR and HRMS, and the synthesized compound 7 is a pure compound, and each performance index or characterization data thereof is as follows:

$[\alpha]_D^{25}$+1.2 (c0.53, CHCl$_3$); $^1$H NMR (400 MHz, CDCl$_3$) δ8.01 (s, 1H), 7.27-7.17 (m, 5H), 6.42 (d, J=8.9 Hz, 1H), 4.96 (dd, J=7.7, 3.8 Hz, 1H), 4.38 (s, 1H), 4.10 (d, J=9.8 Hz, 1H), 3.83 (t, J=9.6 Hz, 1H), 3.62 (s,3H), 2.91 (ddd, J=35.0, 13.9, 6.5 Hz, 2H), 2.68-2.54 (m, 1H), 2.01-1.97 (m, 1H), 1.93-1.75 (m, 5H), 1.60 (ddd, J=14.0, 9.8, 4.2 Hz, 1H), 1.52-1.38 (m, 1H), 1.29 (s, 1H), 1.15 (d, J=7.1 Hz, 3H), 1.04 (d, J=6.9 Hz, 3H), 0.97-0.77 (m, 18H), 0.14 (s, 3H), −0.03 (s, 3H); $^{13}$C NMR (101 MHz, CDCl$_3$) δ176.59, 176.48168.25, 160.71, 149.63, 137.67, 129.50, 128.32, 126.43, 123.08, 70.53, 70.40, 51.67, 51.15, 48.54, 41.07, 38.57, 38.29, 37.66, 36.46, 31.61, 24.22, 18.30, 17.65, 16.01, 11.55, −4.79, −4.96; HR-ESIMS m/z: theoretical calculated value C$_{35}$H$_{56}$N$_6$O$_5$SSiNa$^+$[M+Na]$^+$: 723.3802, detection value: 723.3808.

(4) Synthesis of Compound 9

The compound 7 (2.11 g, 3.0 mmol) is dissolved in the mixed solvent of tetrahydrofuran and water (20:1, 105 mL), the PPh$_3$ (7.9 g, 30 mmol) is added, heating under reflux is performed for reaction with 2 h, vacuum concentration is performed, toluene water washing is performed for three times, and vacuum drying is performed to obtain an intermediate amine.

The intermediate amine is dissolved in the anhydrous DCM (100 mL), the N-Boc-D-piperidine-2-carboxylic acid-compound 8 (0.92 g, 4 mmol) and HATU (3.8 g, 10 mmol) are added and uniformly stirred, then the DIPEA (3.3 mL, 20 mmol) is dropwise added and stirred, and the reaction is carried out overnight at room temperature, water (200 mL) is added for quenching the reaction, extraction is performed with DCM (200 mL) for three times, the extracted organic phases are combined and washed with water (200 mL) and saturated salt water (200 mL) in sequence, the washed organic phases are dried by adding anhydrous sodium sulfate after separating liquid, and vacuum concentration is performed on the dried organic phases to obtain a crude product; and the compound 9 is obtained through rapid column chromatography separation of the crude product by using the eluent of petroleum ether:ethyl acetate being 4:1. The compound 9 is an oil with 2.02 g, and the total yield of the above two steps is 76%.

The synthesized compound 9 is detected by $^1$HNMR, $^{13}$CNMR and HRMS, and the synthesized compound 9 is a pure compound, and each performance index or characterization data thereof is as follows:

$[\alpha]_D^{25}$+13.0 (c0.92, CHCl$_3$); $^1$H NMR (400 MHz, CDCl$_3$) δ8.00 (d, J=5.1 Hz, 1H), 7.25 (dd, J=17.6, 6.4 Hz, 5H), 6.64 (d, J=9.0 Hz, 1H), 6.42 (d, J=8.7 Hz, 1H), 4.92 (dd, J=8.2, 2.8 Hz, 1H), 4.81 (m, 2H), 4.45-4.34 (m, 1H), 4.17 (t, J=8.6 Hz, 1H), 4.08 (s, 1H), 4.03-3.84 (m, 1H), 3.63 (s, 3H), 3.00 (dd, J=13.6, 6.2 Hz, 1H), 2.89 (dd, J=13.9, 7.0 Hz, 1H), 2.81(s, 1H), 2.63 (s, 1H), 2.30 (s, 2H), 2.13-1.75 (m, 6H), 1.69-1.62 (m, 2H), 1.56 (s, 2H), 1.44 (d, J=27.5 Hz, 9H), 1.41 (s, 2H), 1.16 (d, J=7.1 Hz, 3H), 0.97-0.87 (m,21H), 0.17 (s, 3H), −0.03 (s,3H); $^{13}$C NMR (101 MHz, CDCl$_3$) δ176.90, 176.62, 170.82, 160.73, 149.72, 137.77, 129.47, 128.33, 126.42, 123.02, 80.70, 70.46, 58.24, 51.68, 51.37, 48.67, 45.20, 41.97, 41.11, 37.66, 36.48, 35.74, 31.86, 29.64, 28.27, 25.73, 24.64, 21.40, 21.25, 20.47, 18.24, 17.99, 17.88, 17.73, 15.74, 10.87, −4.79; HR-ESIMS m/z: theoretical calculated value C$_{46}$H$_{75}$N$_5$O$_8$SSiNa$^+$[M+Na]$^+$: 908.5106, detection value: 908.5110.

(5) Synthesis of Compound 1 (Final Product Tubulysin U)

The compound 6 (2.02 g, 2.28 mmol) is dissolved in the methanol (40 mL), the ammonium fluoride solid (4.4 g, 120 mmol) is added, heating under reflux is performed for reaction overnight, the vacuum concentration is performed, the water (200 mL) is added for dilution, extraction is performed with ethyl acetate (200 mL) for three times, the extracted organic phases are combined and washed with saturated salt water (200 mL), the washed organic phases are dried by adding anhydrous sodium sulfate after separating liquid, and the vacuum concentration is performed on the dried organic phases to obtain the first intermediate;

The above first intermediate is dissolved in the mixed solvent of tetrahydrofuran and water (1:1, 200 mL), the sodium hydroxide solid (1.2 g, 30 mmol) is added, then heating under reflux is performed for reaction with 10 h, cooling in an ice water bath, the diluted hydrochloric acid is added until the pH of the solution is 2, extraction is performed with ethyl acetate (200 mL) for three times, the extracted organic phases are combined and washed with water (200 mL) and saturated salt water (200 mL) in sequence, the organic phases are dried by adding anhydrous sodium sulfate after separating liquid, and vacuum concentration is performed on the dried organic phases to obtain a second intermediate.

The above second intermediate is dissolved in the pyridine (40 mL), the acetic anhydride (10 mL) is added and stirred for reaction at room temperature with 16 h, the water (400 mL) is added for quenching the reaction, cooling in an ice water bath, then the concentrated hydrochloric acid is added until the pH value of the solution is 2, extraction is performed with ethyl acetate (250 mL) for three times, the extracted organic phases are combined and washed with water (200 mL) and saturated salt water (200 mL) in sequence, the washed organic phases are dried by adding anhydrous sodium sulfate after separating liquid, and vacuum concentration is performed on the dried organic phases to obtain a third intermediate.

The above third intermediate is dissolved in the DCM (50 mL), the TFA (10 mL) is added and stirred for reaction at room temperature with 4 h, the vacuum concentration and vacuum drying are performing to obtain a fourth intermediate.

The fourth intermediate is dissolved in the mixed solvent of methyl cyanide and methanol (1:1, 100 mL), 37% of HCHO (4.0 mL) is added and stirred for reaction at room temperature with 0.5 h, the sodium cyanoborohydride (1.57 g, 25 mmol) is added and stirred for reaction with 0.5 h, glacial acetic acid is dropwise added until the pH of the solution is 5, reaction is performed overnight at room temperature, then the vacuum concentration is performed, and separating and purifying is performed by silica gel column chromatography (mobile phase: methanol:dichloromethane 1:10), and finally pulping and purifying is performed with isopropyl ether to obtain the final product of 11.41 g, and the total yield of the above five steps is 80%.

The synthesized compound 1 is detected by $^1$HNMR, $^{13}$CNMR and HRMS, and the synthesized compound 1 is a pure compound, and each performance index or characterization data thereof is as follows:

$[\alpha]_D^{25}$−10.5 (c0.46, MeOH); $^1$H NMR (400 MHz, MeOD) δ8.10 (s, 1H), 7.29-7.19 (m, 4H), 7.18-7.15 (m,1H), 5.92 (dd, J=10.9, 2.8 Hz, 1H), 4.39-4.32 (m, 1H), 4.23 (d, J=8.2 Hz, 1H), 4.04-3.90 (m, 1H), 3.32-3.20 (m, 2H), 2.93 (d, J=6.7 Hz, 2H), 2.67-2.61 (m, 1H), 2.52 (s, 3H), 2.29-2.21 (m, 1H), 2.16 (s, 3H), 2.13-2.07 (m,1H), 2.02-1.98 (m,1H), 1.93-1.78(m, 4H), 1.79-1.55 (m, 5H), 1.54-1.45 (m,1H), 1.26-1.20 (m, 1H), 1.17 (d, J=7.1 Hz, 3H), 1.00 (d, J=6.8 Hz, 3H), 0.97-0.92 (m, 9H); $^{13}$C NMR (101 MHz, MeOD) δ181.94, 173.66, 172.32, 171.73, 162.73, 150.97, 139.62, 130.47, 129.29, 127.36, 125.01, 71.29, 69.21, 59.79, 56.25, 52.03, 51.00, 43.77, 41.92, 39.19, 38.87, 38.01, 37.59, 33.75, 30.80, 25.85, 25.04, 23.18, 20.75, 19.57, 18.87, 18.59, 16.24, 11.13; HR-ESIMS m/z: theoretical calculated value C$_{37}$H$_{55}$N$_5$O$_7$S$^+$[M+Na]$^+$: 714.3822, detection value: 714.3830.

The compound 6 used in the above preparation process is obtained by the following preparation steps:

Synthesis of Compound 11

The L-phenylalanine 10 (20 g, 132.3 mmol) is dissolved in the mixed solvent of tetrahydrofuran and water (1:1, 800 mL), the sodium bicarbonate (50.4 g, 600 mmol) is added and uniformly stirred, Boc anhydride (its chemical formula is Boc$_2$O) (30 mL, 132 mmol) is dropwise added and stirred for reaction overnight at room temperature, vacuum concentration is performed, water (200 mL) is added for dilution, extraction is performed with ethyl acetate (200 mL) for three times, the extracted organic phases are combined and dried by adding anhydrous sodium sulfate, and vacuum concentration is performed on the dried organic phases to obtain the compound 11, which is directly used for the next step reaction.

Synthesis of Compound 13

The compound 11 (5.0 g, 19.9 mmol) is dissolved in methyl cyanide (200 mL), the IBX (11.2 g, 40 mmol) is added, heating under reflux is performed for reaction with 2 h, cooling to room temperature, filtering, and the filtrate is performed vacuum concentration to obtain an intermediate aldehyde.

The above intermediate aldehyde is dissolved in DCM (300 mL), the compound 12 (8.7 g, 24 mmol) is added and stirred for reaction at room temperature for 14 h, and vacuum concentration is performed to obtain a crude product, and the compound 13 is obtained through rapid column chromatography separation of the crude product by using eluent of petroleum ether:ethyl acetate being 20:1. The compound 13 is a colorless liquid of 4.86 g, and a yield of the above twosteps is 90%. The compound 13 is directly used for the next step reaction.

Among them, the preparation method of the compound 12 refers to the reference document: J. Org. Chem., 2018, 83 (13): 7180-7205.

Synthesis of Compound 14

The compound 13 (4.86 g, 17.9 mmol) is dissolved in methanol (150 mL) and cooled to 0° C. in ice-water bath, then nickel chloride hexahydrate (its chemical formula is $NiCl_2.6H_2O$) (0.86 g, 3.6 mmol) is added and uniformly stirred. After the uniformly stirring, the sodium borohydride (its chemical formula is $NaBH_4$) (2.04 g, 53.7 mmol) is slowly added in batches, and the reaction is continued at 0° C. for 30 min. Saturated ammonium chloride aqueous solution (300 mL) is added for quenching the reaction. The extraction is performed with DCM (200 mL) for three times, the extracted organic phases are combined and washed with water (200 mL) and saturated salt water (200 mL) in sequence, the washed organic phases are dried with anhydrous sodium sulfate after separating liquid, and vacuum concentration is performed on the dried organic phases to obtain the first intermediate.

The first intermediate is dissolved in the mixed solvent of tetrahydrofuran and water (1:1, 300 mL), the sodium hydroxide solid (7.2 g, 180 mmol) is added, then heating under reflux is performed for reaction with 12 h, vacuum concentration is performed, then cooling in an ice water bath, the diluted hydrochloric acid is added until the pH of the solution is equal to 2, extraction is performed with ethyl acetate (200 mL) for three times, the extracted organic phases are combined and washed with water (200 mL) and saturated salt water (200 mL) in sequence, the washed organic phase are dried by adding anhydrous sodium sulfate after separating liquid, and vacuum concentration is performed to obtain a second intermediate.

The above second intermediate is dissolved in the THF (200 mL) and cooled in an ice-water bath, the N-methylmorpholine (abbreviated as NMM) (3.3 mL, 30 mmol) and isobutyl chloroformate (abbreviated as IBCF) (2.3 mL, 18 mmol) are dropwise added for reaction at 0 degree for 30 minutes, the sodium borohydride (2.0 g, 53 mmol) and methanol (50 mL) are added, the temperature is slowly raised to room temperature to react for 2 h, vacuum concentration is performed and water (200 mL) is added for dilution, extraction is performed with ethyl acetate (200 mL) for three times, the extracted organic phases are combined and washed with 1M diluted hydrochloric acid (200 mL) and saturated salt water (200 mL) in sequence, the washed organic phases are dried by adding anhydrous sodium sulfate after separating liquid, and vacuum concentration is performed to obtain a crude product; the compound 14 is obtained by rapid column chromatography separation of the crude product by using the eluent of petroleum ether:ethyl acetate being 4:1. The compound 14 is 3.15 g of the oil, and the total yield of the above three steps is 60%. At the same time, the diastereomer 14' of 1.05 g can be obtained with a total yield of 20% in the above three steps.

The polarities of the compound 14 and the diastereomer 14' have a certain difference, and the retention factor (Rf) values differ by 0.15, and the compound 14 and the diastereomer 14' can be rapidly separated and purified by silica gel column chromatography.

The synthesis method is short in steps, simple in separation and purification, high in total yield and capable of being amplified and prepared.

The synthesized compound 14 is detected by $^1$HNMR, $^{13}$CNMR, HRMS, and the synthesized compound 14 is a pure compound, and each performance indicator or characterization data thereof is as follows:

$[\alpha]_D^{25}$+14.5 (c0.59, $CHCl_3$); $^1$H NMR (400 MHz, $CDCl_3$) δ7.29-7.15 (m, 5H), 4.45 (d, J=7.4 Hz, 1H), 4.03 (s, 1H), 3.47 (d, J=5.8 Hz, 2H), 2.83-2.64 (m, 2H), 2.18 (s, 1H), 1.77 (d, J=6.2 Hz, 1H), 1.53 (ddd, J=12.4, 8.6, 4.5 Hz, 1H), 1.38 (s, 9H), 1.22 (m, 1H), 0.92 (d, J=6.8 Hz, 3H); $^{13}$C NMR (101 MHz, $CDCl_3$) δ155.77, 137.94, 129.42, 128.29, 126.27, 79.27, 67.87, 49.53, 41.67, 39.26, 32.45, 28.32, 17.78; HR-ESIMS m/z: theoretical calculated value $C_{17}H_{27}NO_3Na^+[M+Na]^+$: 316.1991, detection value: 316.2000.

Synthesis of Compound 16

The compound 14 (3.15 g, 10.7 mmol) is dissolved in methyl cyanide (200 mL), the IBX (5.6 g, 20 mmol) is added, heating under reflux is performed for reaction with 2 h, cooling is performed to room temperature, filtration is performed, vacuum concentration is performed on the filtrate to obtain the intermediate 15, and the intermediate 15 is directly used for the next reaction.

The intermediate 15 is dissolved in 6M hydrochloric acid (150 mL), heating under reflux is performed for reaction with 6 h, vacuum concentration is performed, and then pulping and purifying is performed with isopropyl ether to obtain the amino acid compound 16 of 2.1 g, and yield of the above two steps is 80%.

The synthesized compound 16 is detected by $^1$HNMR, $^{13}$CNMR, HRMS, and the synthesized compound 16 is a pure compound, and each performance indicator or characterization data thereof is as follows: M.p. 140-141° C.; $[\alpha]_D^{25}$+4.0 (c1.0, MeOH); $^1$H NMR (400 MHz, $D_2O$) δ7.55-7.25 (m, 5H), 3.68-3.57 (m, 1H), 3.06 (dd, J=14.2, 6.7 Hz, 1H), 2.95 (dd, J=14.2, 7.7 Hz, 1H), 2.72 (dd, J=14.7, 6.9 Hz, 1H), 2.06 (ddd, J=14.6, 8.6, 5.9 Hz, 1H), 1.83-1.68 (m,1H), 1.21 (d, J=7.0 Hz, 3H); $^{13}$C NMR (101 MHz, $D_2O$) δ179.88, 129.46, 129.10, 127.57, 51.26, 38.32, 35.78, 35.44, 16.63; HR-ESIMS m/z: theoretical calculated value $C_{12}H_{17}NO_2^+$ $[M+H]^+$: 209.1259, detection value: 209.1302.

Synthesis of Compound 6

The compound 16 (2.1 g, 8.62 mmol) is dissolved in the absolute methanol (150 mL) and cooled in an ice water bath, the thionyl chloride (it chemical formula is $SOCl_2$) (2.2 mL, 30 mmol) is dropwise added, heating under reflux is performed for reaction with 2 h, vacuum concentration and vacuum drying are performed, and after the vacuum drying, the compound 6 is obtained with a nearly quantitative yield without purification and characterization, and is directly used for the next reaction to prepare the compound 1 (final product Tubulysin U).

The preparation method of the novel natural bioactive peptide Tubulysin U of the present disclosure meets the green chemical standard, utilizes renewable and recyclable resources as much as possible, has less toxicity, and has little environmental pollution after the reaction is treated. In particular, the preparation method has high total yield, good stereoselectivity, convenient experimental operation, mild reaction conditions, simple separation and purification, and can be used for large-scale preparation.

Although embodiments disclosed in the present disclosure are as described above, the contents described herein are merely embodiments used to facilitate understanding of the present disclosure, and are not intended to limit the present disclosure. Any modifications and changes may be made to those skilled in the art without departing from the spirit and scope of the present disclosure, but the scope of the present disclosure still needs to be defined by the scope defined by the appended claims.

What is claimed is:

1. A preparation method of a bioactive peptide Tubulysin U, wherein the bioactive peptide Tubulysin U is prepared through a first route as follows:

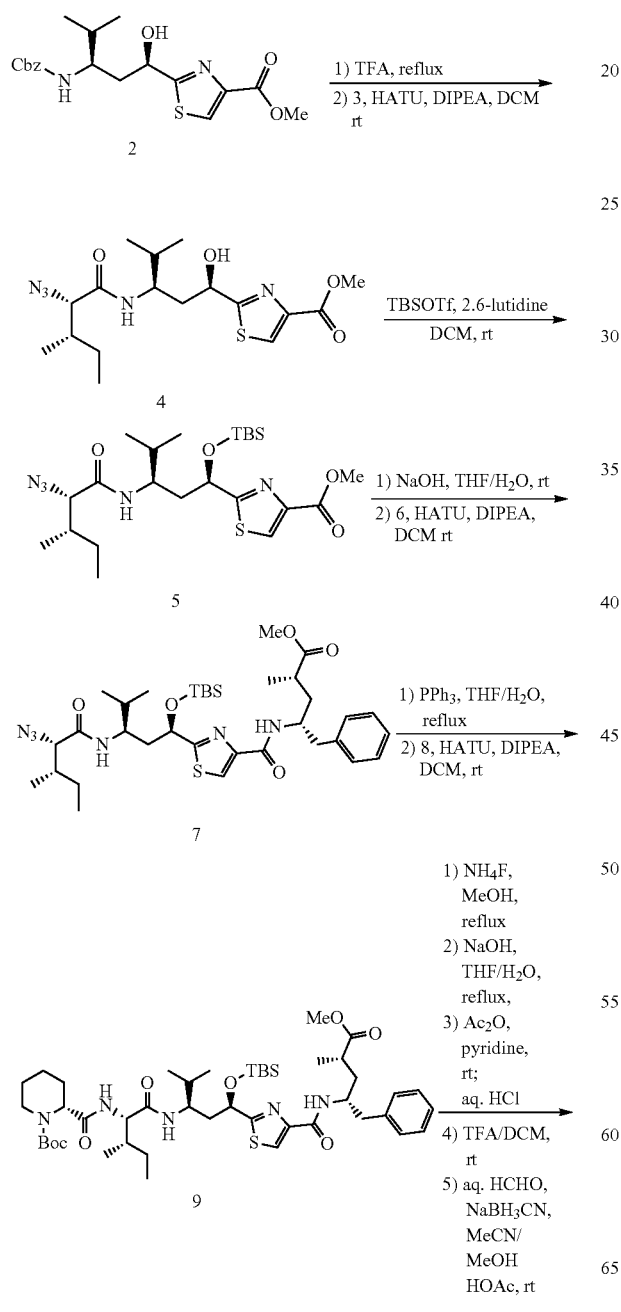

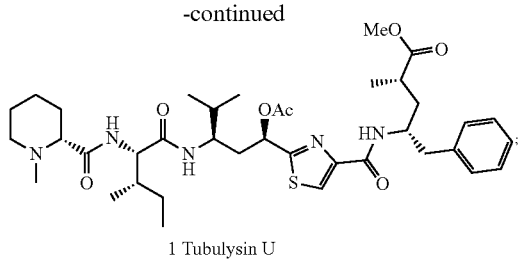

1 Tubulysin U wherein structural formulas of the compound 3, the compound 6 and the compound 8 used in the first route are as follows:

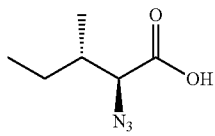

3

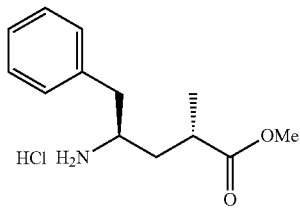

6

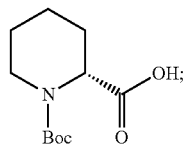

8 wherein the preparation method comprises:

step 1, dissolving the compound 2 in the trifluoroacetic acid (TFA), heating under reflux, and preparing an intermediate;

dissolving the intermediate in the anhydrous dichloromethane (DCM) to obtain first solution, adding the compound 3 and the N,N-diisopropylethylamine (DIPEA) into the first solution for reaction at room temperature to prepare the compound 4;

step 2, dissolving the compound 4 in the dried DCM to obtain second solution, adding the 2,6-lutidine and tert-butyldimethylsilyl trifluoromethanesulfonate (TBSOTf) into the second solution under ice water bath cooling for reaction at room temperature to prepare the compound 5;

step 3: dissolving the compound 5 in the mixed solvent of tetrahydrofuran and water (THF/H₂O) to obtain third solution, adding the sodium hydroxide (NaOH) into the third solution under ice water bath cooling for reaction at room temperature to prepare an intermediate acid;

dissolving the intermediate acid in the anhydrous DCM to obtain fourth solution, adding the compound 6 and the 2-(7-Azabenzotriazol-1-yl)-N,N,N',N'-tetramethyluronium hexafluorophosphate (HATU) into the fourth solution and uniformly stirring, then dropwise adding the DIPEA for reaction at room temperature to prepare the compound 7;

step 4, dissolving the compound 7 in the mixed solvent of tetrahydrofuran and water to obtain fifth solution, adding the triphenylphosphine (PPh$_3$) into the fifth solution, and then heating under reflux, and preparing an intermediate amine;

dissolving the intermediate amine in the anhydrous DCM to obtain sixth solution, adding the compound 8 and the HATU into the sixth solution and uniformly stirring, then dropwise adding the DIPEA for reaction at room temperature to prepare the compound 9;

step 5, dissolving the compound 9 in the methanol (MeOH) to obtain seventh solution, adding the ammonium fluoride (NH$_4$F) into the seventh solution, then heating under reflux overnight, and obtaining a first intermediate after post-treatment;

dissolving the first intermediate in the mixed solvent of tetrahydrofuran and water to obtain eighth solution, adding the sodium hydroxide into the eighth solution, then heating under reflux, and obtaining a second intermediate after post-treatment;

dissolving the second intermediate in the pyridine to obtain ninth solution, then adding the acetic anhydride (Ac$_2$O) into the ninth solution for reaction at room temperature, and obtaining a third intermediate after post-treatment;

dissolving the third intermediate in the DCM to obtain tenth solution, then adding the trifluoroacetic acid (TFA) into the tenth solution for reaction at room temperature, and obtaining a fourth intermediate after post-treatment;

dissolving the fourth intermediate in the mixed solvent of methyl cyanide and methanol (MeCN/MeOH) to obtain eleventh solution, adding the formaldehyde (HCHO) into the eleventh solution for reaction at room temperature, then adding the sodium cyanoborohydride (NaBH$_3$CN) to continue the reaction, and obtaining the bioactive peptide Tubulysin U after post-treatment.

2. The preparation method of the bioactive peptide Tubulysin U according to claim 1, wherein the compound 6 is synthesized through a second route as follows:

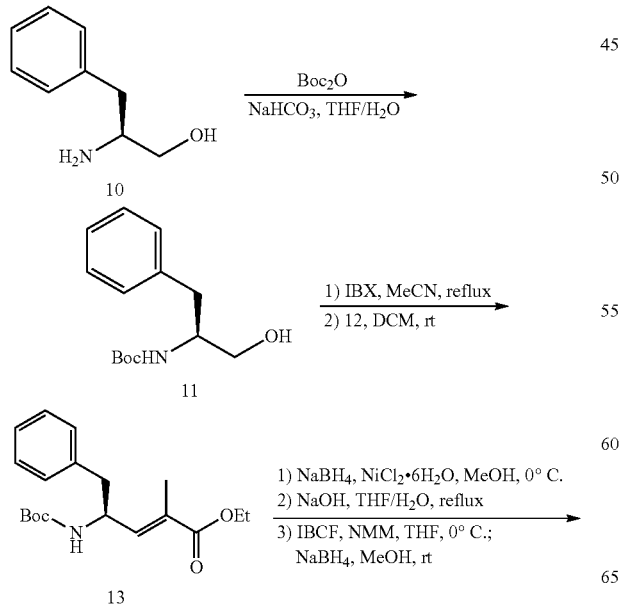

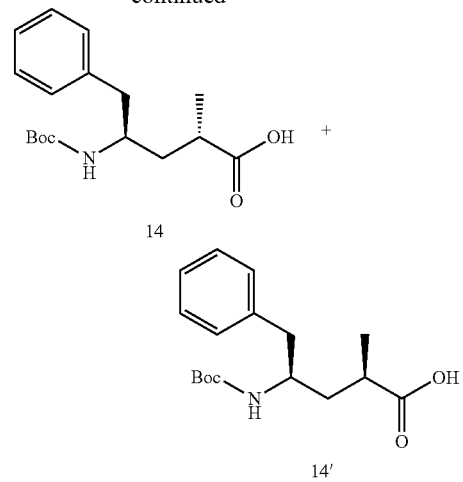

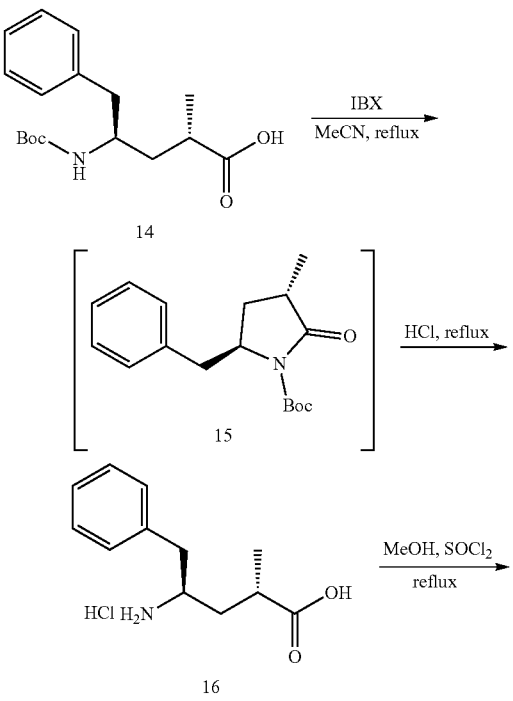

wherein a structural formula of the compound 12 used in the second route is as follows:

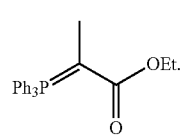

3. The preparation method of the bioactive peptide Tubulysin U according to claim 1, wherein the step 1 comprises:
   step 11: dissolving the compound 2 in the TFA, then heating under reflux and performing vacuum concentration to obtain the intermediate;
   step 12: dissolving the intermediate in the anhydrous DCM to obtain the first solution, adding the compound 3 into the first solution and uniformly stirring, then dropwise adding the DIPEA and stirring for the reaction at room temperature, quenching the reaction after the reaction is completed, extracting organic phases with DCM and combining the extracted organic phases, washing the combined organic phases with water and saturated salt water in sequence, collecting and drying the washed organic phases, concentrating the dried organic phases, and separating the concentrated organic phases through column chromatography to obtain the compound 4.

4. The preparation method of the bioactive peptide Tubulysin U according to claim 3, wherein in the step 1, time of the heating under reflux is in a range of 2 hours (h) to 4 h.

5. The preparation method of the bioactive peptide Tubulysin U according to claim 3, wherein in the step 1, a molar ratio of the compound 2:the compound 3:the HATU:the DIPEA is 1:1.1-1.4:2-3:4-5.

6. The preparation method of the bioactive peptide Tubulysin U according to claim 3, wherein in the step 12, the concentrated organic phases are separated through the column chromatography by using eluent of a volume ratio of petroleum ether:ethyl acetate being 4:1.

7. The preparation method of the bioactive peptide Tubulysin U according to claim 1, wherein the step 2 comprises:
   dissolving the compound 4 in the dried DCM to obtain the second solution, adding the 2,6-lutidine and the TBSOTf into the second solution under ice-water bath cooling, then heating to room temperature for the reaction, adding water for quenching the reaction after the reaction is completed, extracting organic phases with DCM and combining the extracted organic phases, washing the combined organic phases with diluted hydrochloric acid and saturated salt water in sequence, collecting the washed organic phases by liquid separation and drying the collected organic phases by anhydrous sodium sulfate, and concentrating the dried organic phases, and separating the concentrated organic phases through column chromatography to obtain the compound 5.

8. The preparation method of the bioactive peptide Tubulysin U according to claim 7, wherein a molar ratio of the compound 4:the 2,6-lutidine:the TBSOTf is 1:3-4:1.2-2.

9. The preparation method of the bioactive peptide Tubulysin U according to claim 7, wherein in the step 2, the concentrated organic phases are separated through the column chromatography separation by using eluent with a volume ratio of petroleum ether:ethyl acetate being 8:1.

10. The preparation method of bioactive peptide Tubulysin U according to claim 1, wherein the step 3 comprises:
   dissolving the compound 5 in the mixed solvent of tetrahydrofuran and water to obtain the third solution, adding the sodium hydroxide into the third solution under ice-water bath cooling, heating to room temperature and stirring for the reaction, then cooling in ice water bath and adjusting pH of reaction solution to 2, extracting first organic phases with ethyl acetate and combining the extracted first organic phases, washing the combined first organic phases with water and saturated salt water in sequence, drying the washed first organic phases by adding anhydrous sodium sulfate after separating liquid, and performing vacuum concentration on the dried first organic phases to obtain the intermediate acid;
   dissolving the intermediate acid in the anhydrous DCM to obtain the fourth solution, adding the compound 6 and the HATU into the fourth solution and uniformly stirring, then dropwise adding the DIPEA and stirring for the reaction at room temperature, adding water for quenching the reaction after the reaction is completed, extracting second organic phases with dichloromethane and combining the extracted second organic phases, washing the combined second organic phases with water and saturated salt water in sequence, drying the washed second organic phases by adding anhydrous sodium sulfate after separating liquid, performing vacuum concentration on the dried second organic phases, and then performing column chromatography separation on the concentrated second organic phases with eluent of petroleum ether:ethyl acetate being 6:1 to obtain the oily compound 7.

11. The preparation method of the bioactive peptide Tubulysin U according to claim 10, wherein a volume ratio of the tetrahydrofuran: the water in the mixed solvent of tetrahydrofuran and water is 1:1; and/or
   wherein a molar ratio of the compound 5:the compound 6:the HATU:the DIPEA is 1:1.1-1.5:2-3:4-5.

12. The preparation method of the bioactive peptide Tubulysin U according to claim 1, wherein the step 4 comprises:
   dissolving the compound 7 in the mixed solvent of tetrahydrofuran and water to obtain the fifth solution, adding the PPh$_3$ into the fifth solution, then heating under reflux and performing vacuum concentration, subsequently washing with toluene to remove water, and performing vacuum drying to obtain the intermediate amine;
   dissolving the intermediate amine in the anhydrous DCM to obtain the sixth solution, adding the compound 8 and the HATU into the sixth solution and uniformly stirring, then dropwise adding the DIPEA and stirring for the reaction at room temperature, adding water for quenching the reaction after the reaction is completed, extracting organic phases with DCM and combining the extracted organic phases, washing the combined organic phases with water and saturated salt water in sequence, drying the washed organic phases by adding anhydrous sodium sulfate after separating liquid, performing vacuum concentration on the dried organic phases, and then performing column chromatography separation on the concentrated organic phases by using petroleum ether and ethyl acetate as eluent to obtain the oily compound 9.

13. The preparation method of the bioactive peptide Tubulysin U according to claim 12, wherein a molar ratio of the compound 7:the compound 8:the HATU:the DIPEA is 1:1.1-1.5:2-3:4-6; and/or
   wherein in the step 4, a volume ratio of the tetrahydrofuran: the water in the mixed solvent of tetrahydrofuran and water is 20:1; and/or
   wherein in the step 4, time of the heating under reflux is in a range from 1.5 h to 2.5 h.

14. The preparation method of the bioactive peptide Tubulysin U according to claim 1, wherein the step 5 comprises:
dissolving the compound 9 in the methanol to obtain the seventh solution, adding the ammonium fluoride solid into the seventh solution, then heating under reflux overnight and performing vacuum concentration, subsequently adding water for dilution, extracting first organic phases with ethyl acetate and combining the extracted first organic phases, washing the combined first organic phases with saturated salt water, drying the washed first organic phases by adding anhydrous sodium sulfate after separating liquid, and performing vacuum concentration on the dried first organic phases to obtain the first intermediate;
dissolving the first intermediate in the mixed solvent of tetrahydrofuran and water with a volume ratio of the tetrahydrofuran:the water being 1:1 to obtain the eight solution, adding the sodium hydroxide into the eight solution, then heating under reflux, cooling in ice water bath and adjusting pH of reaction solution to 2, then extracting second organic phases with ethyl acetate and combining the extracted second organic phases with ethyl acetate, washing the combined second organic phases with water and saturated salt water in sequence, drying the washed second organic phases with anhydrous sodium sulfate after separating liquid, and performing vacuum concentration on the dried second organic phases to obtain the second intermediate;
dissolving the second intermediate in the pyridine to obtain the ninth solution, then adding the acetic anhydride into the ninth solution and stirring for the reaction at room temperature, adding water for quenching the reaction after the reaction is completed, cooling in an ice water bath and adjusting pH of reaction solution to 2, extracting third organic phases with ethyl acetate and combining the extracted third organic phases, washing the combined third organic phases with water and saturated salt water in sequence, drying the washed third organic phases with anhydrous sodium sulfate after separating liquid, and performing vacuum concentration on the dried third organic phases to obtain the third intermediate;
dissolving the third intermediate in the DCM to obtain the tenth solution, adding the TFA into the tenth solution and stirring for reaction at room temperature, then performing vacuum concentration and vacuum drying to obtain the fourth intermediate;
dissolving the fourth intermediate in the mixed solvent of methyl cyanide and methanol with a volume ratio of the methyl cyanide:the methanol being 1:1 to obtain the eleventh solution, adding the formaldehyde into the eleventh solution and stirring for the reaction at room temperature, then adding the sodium cyanoborohydride to continue the reaction, adjusting pH of reaction solution to 5, then stirring the reaction solution at room temperature overnight, performing vacuum concentration on the reaction solution, separating and purifying the concentrated reaction solution with silica gel column chromatography, and then pulping and purifying with isopropyl ether to obtain the bioactive peptide Tubulysin U.

15. The preparation method of the bioactive peptide Tubulysin U according to claim 14, wherein a molar ratio of the compound 9:the ammonium fluoride is 1:50; and/or
wherein a molar ratio of the first intermediate:the sodium hydroxide is 1:10; and/or wherein a molar ratio of the second intermediate:the acetic anhydride is 1:50.

16. The preparation method of the bioactive peptide Tubulysin U according to claim 14, wherein, in the step 5, the separating and purifying through the silica gel column chromatography use a mobile phase with a volume ratio of methanol:dichloromethane being 1:10.

17. The preparation method of the bioactive peptide Tubulysin U according to claim 14, wherein a concentration of the formaldehyde is 37 weight percent (wt %).

18. The preparation method of the bioactive peptide Tubulysin U according to claim 1, wherein the compound 2 is prepared through a method as follows:

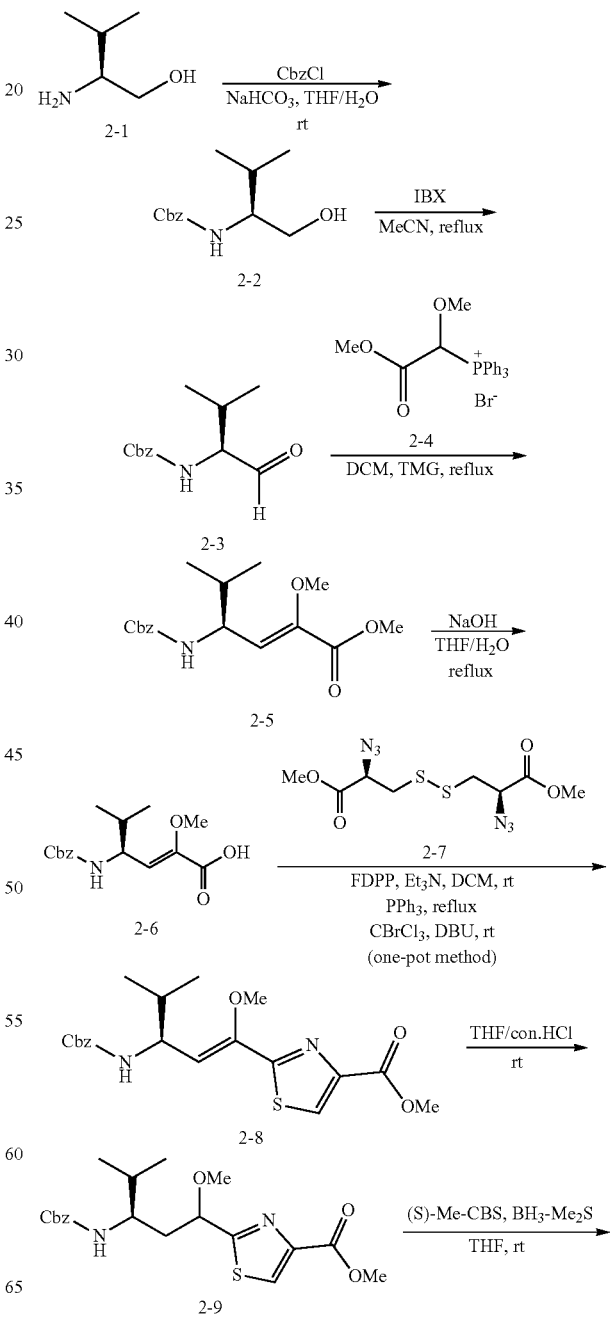

-continued

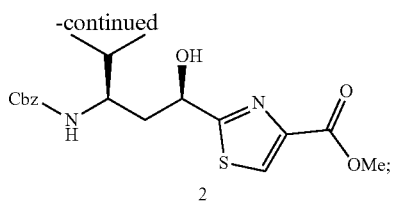

2 wherein the method includes the following steps:

step 1, dissolving initial raw material L-valine 2-1 in the mixed solvent of tetrahydrofuran and water, adding the sodium bicarbonate (NaHCO$_3$) and the benzyl chloroformate (CbzCl) for reaction overnight at room temperature to obtain the compound 2-2;

step 2: dissolving the compound 2-2 in the methyl cyanide (MeCN), adding the 2-iodoxybenzoic acid (IBX), then heating under reflux, and obtaining the intermediate aldehyde 2-3;

dissolving the intermediate aldehyde 2-3 in the DCM, adding the Wittig reagent 2-4 and the 1,1,3,3-tetramethylguanidine (TMG), then heating under reflux, and obtaining the compound 2-5;

step 3, dissolving the compound 2-5 in the mixed solvent of tetrahydrofuran and water, adding the sodium hydroxide, then heating under reflux, and obtaining the compound 2-6;

taking the compound 2-6 as a reaction substrate, adding the perfluorophenyl diphenylphosphinate (FDPP), the triethylamine (Et$_3$N) and the PPh$_3$ to react with the compound 2-7 to prepare a thiazoline intermediate, then adding 1,8-Diazabicyclo[5.4.0]undec-7-ene (DBU) and the bromotrichloromethane (CBrCl$_3$) into the thiazoline intermediate to synthetize the compound 2-8 by a one-pot method;

step 4, dissolving the compound 2-8 in the tetrahydrofuran (THF), then adding concentrated hydrochloric acid (HCl) for reaction at room temperature to obtain a compound 2-9;

step 5: dissolving the compound 2-9 in the anhydrous THF under inert gas protection, adding (S)-Me-CBS and borane dimethyl sulfide complex (BH$_3$-Me$_2$-S) under ice water bath cooling, and then heating to room temperature for reaction to obtain the compound 2.

19. The preparation method of the bioactive peptide Tubulysin U according to claim 18, wherein in the method for preparing the compound 2:

in the step 1, a molar ratio of the L-valine 2-1:the sodium bicarbonate:the benzyl chloroformate is 1:3-5:1-1.02; and/or in the step 2, a molar ratio of the compound 2-2:the 2-iodoxybenzoic acid:the Wittig reagent 2-4 is 1:2-3: 1.2-1.5.

20. The preparation method of the bioactive peptide Tubulysin U according to claim 19, wherein in the method for preparing the compound 2:

in the step 1, time of the reaction is in a range from 10 h to 15 h, after the reaction is completed, vacuum concentration is performed, ethyl acetate is used for extraction, organic phases are combined and washed with saturated salt water, the washed organic phases are collected by liquid separation, then the collected organic phases are dried by adding anhydrous sodium sulfate, the dried organic phases are filtered, concentrated and drained, and the compound 2-2 is obtained.

* * * * *